(12) United States Patent
Zaidy et al.

(10) Patent No.: US 12,354,649 B2
(45) Date of Patent: *Jul. 8, 2025

(54) SIGNAL ROUTING BETWEEN MEMORY DIE AND LOGIC DIE FOR PERFORMING OPERATIONS

(71) Applicant: Micron Technology, Inc., Boise, ID (US)

(72) Inventors: Aliasger T. Zaidy, Seattle, WA (US); Sean S. Eilert, Penryn, CA (US); Glen E. Hush, Boise, ID (US); Kunal R. Parekh, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 297 days.

This patent is subject to a terminal disclaimer.

(21) Appl. No.: 17/885,325

(22) Filed: Aug. 10, 2022

(65) Prior Publication Data

US 2023/0051126 A1 Feb. 16, 2023

Related U.S. Application Data

(60) Provisional application No. 63/231,660, filed on Aug. 10, 2021.

(51) Int. Cl.
*G11C 11/4093* (2006.01)
*G06F 3/06* (2006.01)
(Continued)

(52) U.S. Cl.
CPC ........ *G11C 11/4093* (2013.01); *G06F 3/0656* (2013.01); *G06F 13/1673* (2013.01); *G06F 13/28* (2013.01); *G11C 7/08* (2013.01); *G11C 7/1039* (2013.01); *G11C 11/4087* (2013.01); *G11C 11/4091* (2013.01); *G11C 11/4096* (2013.01); *G16B 30/00* (2019.02); *G16B 50/10* (2019.02); *H01L 21/78* (2013.01); *H01L 22/12* (2013.01); *H01L 24/08* (2013.01); *H01L 24/48* (2013.01); *H01L 24/80* (2013.01); *H01L 25/0652* (2013.01); *H01L 25/0657* (2013.01); *H01L 25/18* (2013.01); *H01L 25/50* (2013.01); *G06F 2213/28* (2013.01);
(Continued)

(58) Field of Classification Search
CPC ........... G11C 11/4093; G11C 11/4087; G11C 11/4091; G11C 11/4096
See application file for complete search history.

(56) References Cited

U.S. PATENT DOCUMENTS 9,344,091 B2 5/2016 Jayasena et al.
9,577,644 B2 2/2017 Gao et al.
(Continued)

*Primary Examiner* — Alfredo Bermudez Lozada
(74) *Attorney, Agent, or Firm* — Brooks, Cameron & Huebsch, PLLC

(57) ABSTRACT

A memory device includes a memory die bonded to a logic die. A logic die that is bonded to a memory die via a wafer-on-wafer bonding process can receive signals indicative of input data from a global data bus of the memory die and through a bond of the logic die and memory die. The logic die can also receive signals indicative of kernel data from local input/output (LIO) lines of the memory die and through the bond. The logic die can perform a plurality of operations at a plurality of vector-vector (VV) units utilizing the signals indicative of input data and the signals indicative of kernel data.

8 Claims, 10 Drawing Sheets

(51) Int. Cl.

| | |
|---|---|
| *G06F 13/16* | (2006.01) |
| *G06F 13/28* | (2006.01) |
| *G11C 7/08* | (2006.01) |
| *G11C 7/10* | (2006.01) |
| *G11C 11/408* | (2006.01) |
| *G11C 11/4091* | (2006.01) |
| *G11C 11/4096* | (2006.01) |
| *G16B 30/00* | (2019.01) |
| *G16B 50/10* | (2019.01) |
| *H01L 21/66* | (2006.01) |
| *H01L 21/78* | (2006.01) |
| *H01L 23/00* | (2006.01) |
| *H01L 25/00* | (2006.01) |
| *H01L 25/065* | (2023.01) |
| *H01L 25/18* | (2023.01) |

(52) U.S. Cl.
CPC ...... *H01L 24/16* (2013.01); *H01L 2224/0801* (2013.01); *H01L 2224/08145* (2013.01); *H01L 2224/1601* (2013.01); *H01L 2224/16221* (2013.01); *H01L 2224/48091* (2013.01); *H01L 2224/48145* (2013.01); *H01L 2224/48221* (2013.01); *H01L 2224/80895* (2013.01); *H01L 2224/80896* (2013.01); *H01L 2225/06517* (2013.01); *H01L 2225/06524* (2013.01); *H01L 2225/06527* (2013.01); *H01L 2225/06541* (2013.01); *H01L 2225/06565* (2013.01); *H01L 2225/06589* (2013.01); *H01L 2924/1431* (2013.01); *H01L 2924/14335* (2013.01); *H01L 2924/1436* (2013.01)

(56) References Cited

U.S. PATENT DOCUMENTS

| | | | |
|---|---|---|---|
| 9,972,611 | B2 | 5/2018 | Pappu et al. |
| 11,430,766 | B2 | 8/2022 | Liu et al. |
| 12,112,793 | B2 * | 10/2024 | Zaidy ................ G11C 11/4096 |
| 2017/0263306 | A1 | 9/2017 | Murphy et al. |
| 2020/0243486 | A1 | 7/2020 | Quader et al. |

* cited by examiner

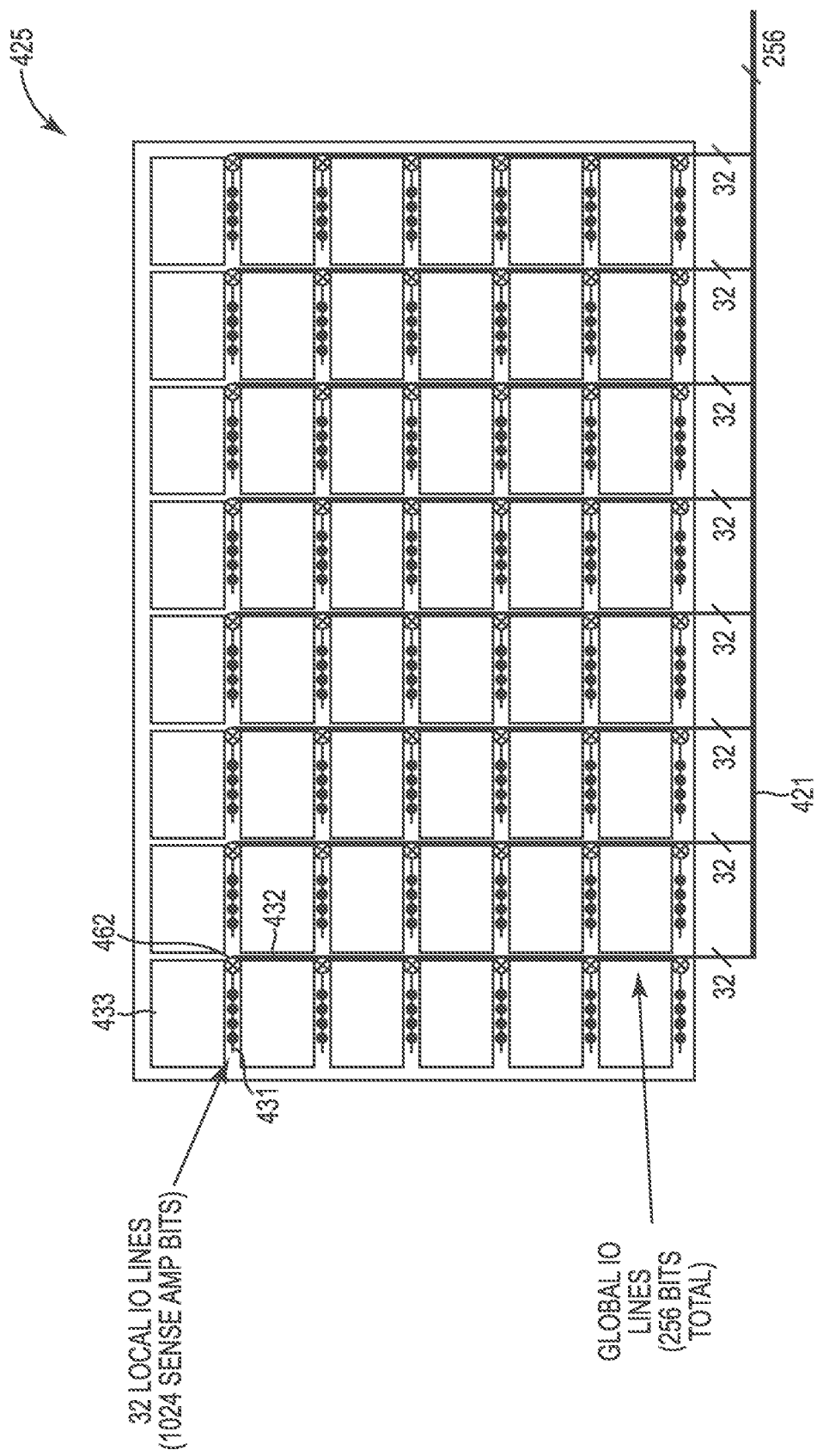

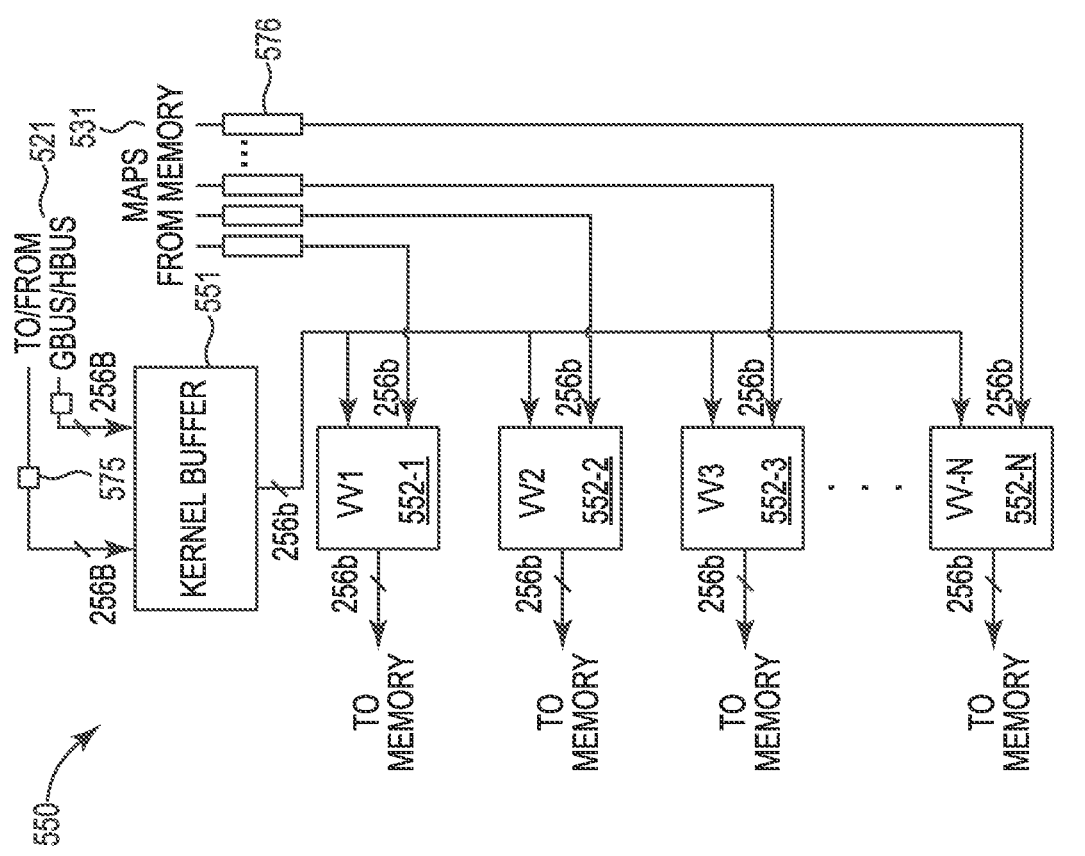

SIGNAL ROUTING BETWEEN MEMORY DIE AND LOGIC DIE FOR PERFORMING OPERATIONS

PRIORITY INFORMATION

This application is a non-provisional Application of U.S. Application No. 63/231,660, filed Aug. 10, 2021, the contents of which are included herein by reference.

TECHNICAL FIELD

The present disclosure relates generally to memory, and more particularly to apparatuses and methods associated with a memory device for routing signals between a memory die and a logic die for performing operations.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random access memory (DRAM), and synchronous dynamic random access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random access memory (PCRAM), resistive random access memory (RRAM), and magnetoresistive random access memory (MRAM), among others.

Memory is also utilized as volatile and non-volatile data storage for a wide range of electronic applications. including, but not limited to personal computers, portable memory sticks, digital cameras, cellular telephones, portable music players such as MP3 players, movie players, and other electronic devices. Memory cells can be arranged into arrays, with the arrays being used in memory devices.

BRIEF DESCRIPTION OF THE DRAWINGS

FIG. 4 illustrates a circuit diagram of a memory bank in accordance with a number of embodiments of the present disclosure.

FIG. 5B illustrates a block diagram of vector-vector circuitry for performing multiplication operations in accordance with a number of embodiments of the present disclosure.

DETAILED DESCRIPTION

Figure 1:
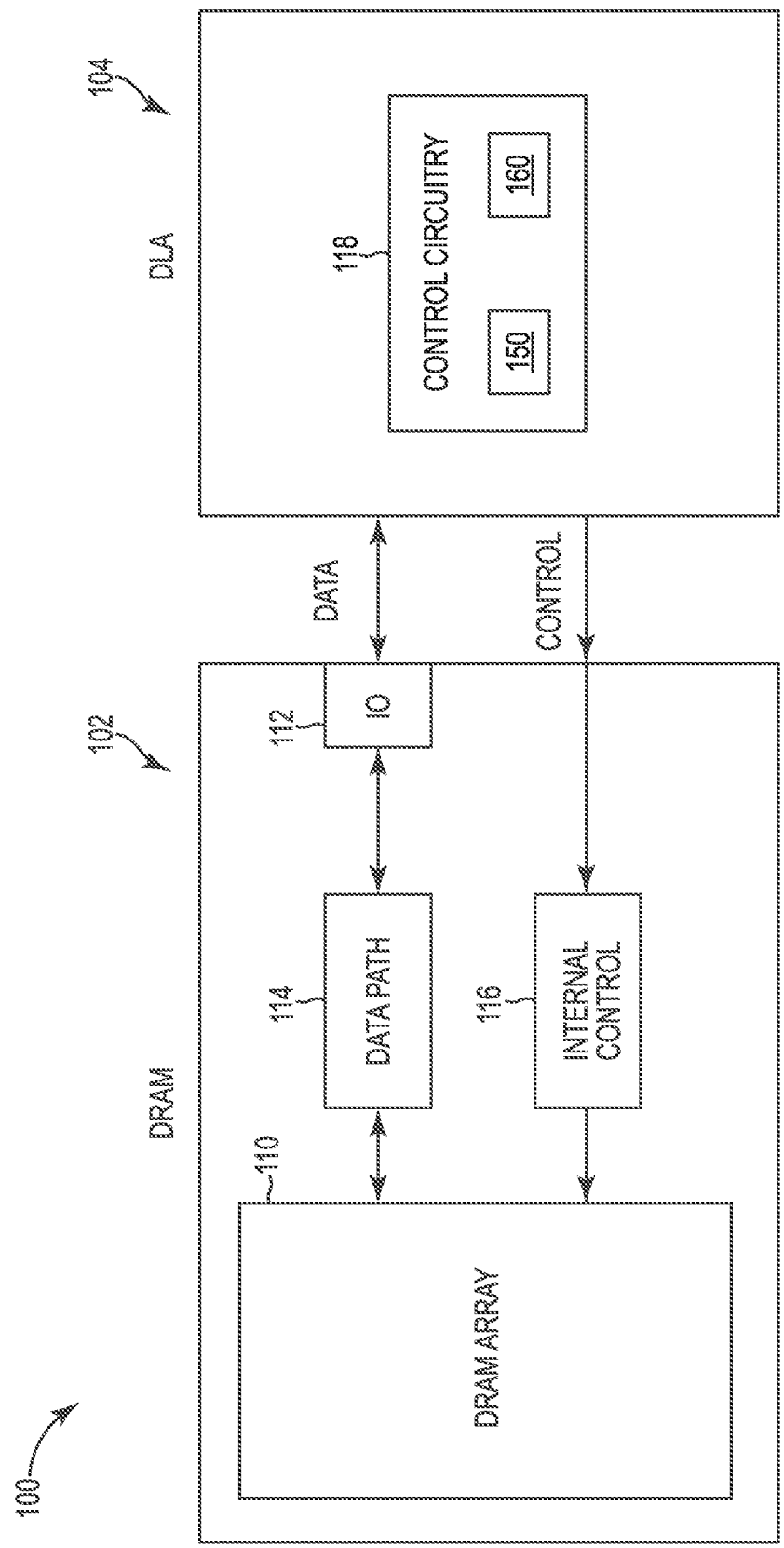
FIG. 1 illustrates a block diagram of an apparatus in the form of a system including a memory device and a logic device in accordance with a number of embodiments of the present disclosure.

The present disclosure includes apparatuses and methods related to a memory device for routing signals between a memory die and a logic die for performing operations. Inexpensive and energy-efficient logic devices have been proposed. Such devices can benefit from being tightly coupled to memory devices. Logic devices can be accelerators. Accelerators can include artificial intelligence (AI) accelerators such as deep learning accelerators (DLAs).

AI refers to the ability to improve a machine through "learning" such as by storing patterns and/or examples which can be utilized to take actions at a later time. Deep learning refers to a device's ability to learn from data provided as examples. Deep learning can be a subset of AI. Neural networks, among other types of networks, can be classified as deep learning. The low power, inexpensive design of deep learning accelerators can be implemented in internet-of-things (IOT) devices. The DLAs can process and make intelligent decisions at run-time. Memory devices including the edge DLAs can also be deployed in remote locations without cloud or offloading capability. Deep learning can be implemented utilizing multiplication operations.

A three-dimensional integrated circuit (3D IC) is a metal-oxide semiconductor (MOS) IC manufactured by stacking semiconductor wafers or dies and interconnecting them vertically using, for example, through-silicon vias (TSVs) or metal connections, to function as a single device to achieve performance improvements at reduced power and smaller footprint than conventional two-dimensional processes. Examples of 3D ICs include hybrid memory cube (HMC) and high bandwidth memory (HBM), among others.

Implementing a memory device that couples memory die and logic die using 3D IC can benefit from the efficient transfer of data between the memory die and the logic die. Transferring data from the memory die to the logic die can include transferring data from the memory die to a global data bus and transferring the data from the global data bus to the logic die. However, transferring data from the global data bus to the logic die can be inefficient.

Aspects of the present disclosure address the above and other deficiencies. For instance, at least one embodiment of the present disclosure can provide high bandwidth via a wide bus between a memory die and a logic die bonded via a wafer-on-wafer bonding process. The bus between the memory die and the logic die can be implemented such that data is transferred to the logic die without going through a traditional I/O. Transferring data, between the memory die and the logic die, using the wide bus, can be more efficient than transferring data via the global data bus."

In various instances, the data can be transferred between the memory die and the logic die using transceivers. The transceivers used to transfer data between the memory die and the logic die can be located on the memory die or can be located on the logic die. The transceivers can allow signal to flow from the memory die to the logic die regardless of whether the transceivers are located on the memory die or the logic die.

The wide bus can be utilized to provide data from the memory device to the logic device to perform multiplication operations. The multiplication operations can be utilized to implement deep learning. Performing multiplication operations utilizing data provided by the wide bus can be more efficient than only utilizing data provided from the global data bus. In various instances, multiplication operations can be performed using data routed from the wide bus and the global data bus.

The figures herein follow a numbering convention in which the first digit or digits correspond to the drawing figure number and the remaining digits identify an element or component in the drawing. Similar elements or components between different figures may be identified by the use of similar digits. For example, 100 references element "00" in FIG. 1, and a similar element is referenced as 200 in FIG. 2. Analogous elements within a Figure may be referenced with a hyphen and extra numeral or letter. See, for example, elements 552-1, 552-2 in FIG. 5. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention and should not be taken in a limiting sense.

FIG. 1 illustrates a block diagram of an apparatus in the form of a system 100 including a memory device 102 and a logic device 104 in accordance with a number of embodiments of the present disclosure. As used herein, a memory device 102, memory array 110, and/or a logic device 104, for example, might also be separately considered an "apparatus."

In this example, the system 100 includes a memory device 102 coupled to the logic device 104 via an interface 112 (e.g., an input/output "TO" interface). The system 100 can be part of a personal laptop computer, a desktop computer, a digital camera, a mobile telephone, a memory card reader, a server, or an Internet-of-Things (IoT) enabled device among various other types of systems. The system 100 can include separate integrated circuits, or both the memory device 102 and the logic device 104 can be on the same integrated circuit. The logic device 104 can be an artificial intelligence (AI) accelerator, which is also referred to herein as a deep learning accelerator (DLA) as an example. The logic device 104 can be referred to herein as a DLA 104. The DLA 104 can be implemented on an edge of the system 100. For example, the DLA 104 can be implemented external to the memory device 102. The DLA 104 can be coupled to the TO circuitry 112 and thus to a data path 114, which is coupled to the memory array 110.

In various examples, the DLA 104 can be bonded to the memory device 102. For example, a memory die of the memory device 102 can be bonded to a logic die of the DLA 104. The memory die of the memory device 102 can be referred to as memory die 102. The logic die of the DLA 104 can be referred to as logic die 102. The logic die 104 can include control circuitry 118. The control circuitry 118 can control the memory device 102 and/or the DLA 104 to route data from the memory die 102 to the logic die 104 via the TSVs that couple the memory die to the logic die. In various instances, the control circuitry 118 can also control the performance of operations on the logic die 104 utilizing circuitry 150 or circuitry 160 referred to as vector-vector circuitry, vector-matrix circuitry, and/or a matrix-matrix unit. For example, the control circuitry 118 can direct the execution of multiplication operations. The multiplication operations can be used, for example, to implement a DLA including an artificial network (e.g., an artificial neural network) among other implementations of a DLA.

For clarity, the system 100 has been simplified to focus on features with particular relevance to the present disclosure. The memory array 110 can be a DRAM array, SRAM array, STT RAM array, PCRAM array, TRAM array, RRAM array, NAND flash array, NOR flash array, and/or 3D cross-point array for instance. The memory array 110 is referred to herein as a DRAM array as an example. The array 110 can comprise memory cells arranged in rows coupled by access lines (which may be referred to herein as word lines or select lines) and columns coupled by sense lines (which may be referred to herein as digit lines or data lines). Although the memory array 110 is shown as a single memory array, the memory array 110 can represent a plurality of memory arrays arranged in banks of the memory device 102.

Although not specifically illustrated, the memory device 102 includes address circuitry to latch address signals provided over a host interface. The host interface can include, for example, a physical interface (e.g., a data bus, an address bus, and a command bus, or a combined data/address/command bus) employing a suitable protocol. Such protocol may be custom or proprietary, or the host interface may employ a standardized protocol, such as Peripheral Component Interconnect Express (PCIe), Gen-Z interconnect, cache coherent interconnect for accelerators (CCIX), or the like. Address signals are received and decoded by a row decoder and a column decoder to access the memory array 110. Data can be read from memory array 110 by sensing voltage and/or current changes on the sense lines using sensing circuitry. The sensing circuitry can be coupled to the memory array 110. Each memory array 110 and corresponding sensing circuitry can constitute a bank of the memory device 102. The sensing circuitry can comprise, for example, sense amplifiers that can read and latch a page (e.g., row) of data from the memory array 110. The IO circuitry 112 can be used for bi-directional data communication with the logic device 104 along a data path 114. Read/write circuitry is used to write data to the memory array 110 or read data from the memory array 110. The read/write circuitry can include various drivers, latch circuitry, etc.

The control circuitry 116 (e.g., internal control) can decode signals provided by the host. The signals can be commands provided by the host. These signals can include chip enable signals, write enable signals, and address latch signals that are used to control operations performed on the memory array 110, including data read operations, data write operations, and data erase operations. In various embodiments, the control circuitry 116 is responsible for executing instructions from the host. The control circuitry 116 can comprise a state machine, a sequencer, and/or some other type of control circuitry, which may be implemented in the form of hardware, firmware, or software, or any combination of the three. In some examples, the host can be a controller external to the memory device 102. For example, the host can be a memory controller which is coupled to a processing resource of a computing device. Data can be provided to the logic device 104 and/or from the logic device 104 via data lines coupling the logic device 104 to the IO circuitry 112.

The DLA 104 can also be coupled to the control circuitry 116. The control circuitry 116 can control the DLA 104. For example, the control circuitry 116 can provide signaling to the row decoder and the column decoder to cause the transferring of data from the memory array 102 to the DLA 104 to provide an input to the DLA 104 and/or a network (e.g., an artificial neural network (ANN)) which is hosted by the DLA 104. The control circuitry 116 can also cause the output of the DLA 104 and/or the network to be provided to the IO circuitry 112 and/or be stored back to the memory array 110.

A network (e.g., network model) can be trained by the DLA 104, the control circuitry 116, and/or by the external host (not specifically illustrated). For example, the host and/or the control circuitry 116 can train the network model which can be provided to the DLA 104. The DLA 104 can utilize the trained network model to implement a network directed by the control circuitry 116. The network model can be trained to perform a desired function.

After fabrication of the electronic devices (e.g., memory device 102 and DLA 104) on a first wafer and a second wafer, the first wafer and the second wafer can be diced (e.g., by a rotating saw blade cutting along streets of the first wafer and the second wafer). However, according to at least one embodiment of the present disclosure, after fabrication of the devices on the first wafer and the second wafer, and prior to dicing, the first wafer and the second wafer can be bonded together by a wafer-on-wafer bonding process. Subsequent to the wafer-on-wafer bonding process, the dies (e.g., memory die and logic die) can be singulated. For example, a memory wafer can be bonded to a logic wafer in a face-to-face orientation meaning that their respective substrates (wafers) are both distal to the bond while the memory dies and logic dies are proximal to the bond. This enables individual memory die and logic die to be singulated together as a single package after the memory wafer and the logic wafer are bonded together.

Figure 2A:
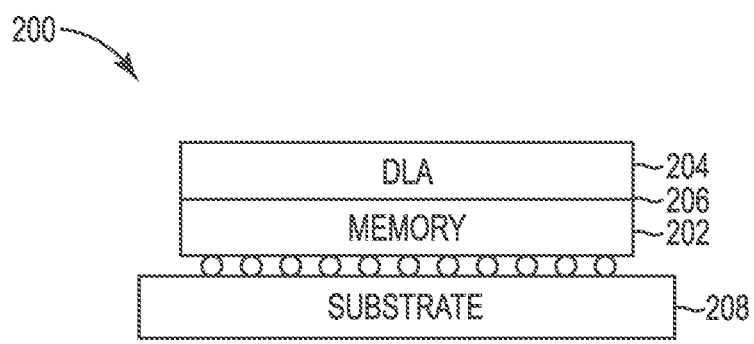
FIG. 2A illustrates a portion of bonded wafers including a memory die and a logic die in accordance with a number of embodiments of the present disclosure.

FIG. 2A illustrates a portion of the bonded wafers including a memory die 202 and a logic die 204 in accordance with a number of embodiments of the present disclosure. The memory die 202 is illustrated as being bonded to a substrate 208, however, in at least one embodiment, the logic die 204 (e.g., DLA 204) can be bonded to the substrate 208 instead of the memory die 202. The substrate 208, memory die 202, bond 206, and logic die 204 can form a system 200, such as an integrated circuit, configured to perform one or more desired functions. Although not specifically illustrated, the substrate 208 can include additional circuitry to operate, control, and/or communicate with the memory die 202, logic die 204, and or other off-chip devices.

According to at least one embodiment of the present disclosure, the typical functionality of the memory die 202 does not change for typical memory operations. However, data can alternatively be transferred from the memory die 202 to the logic die 204 directly via the bond 206 instead of being routed through the typical input/output circuitry of the memory die 202. For example, a test mode and/or refresh cycle of the memory die 202 can be used to transfer data to and from the logic die 204 via the bond 206 (e.g., via LIOs of the memory die 202). Using the refresh cycle for an example existing DRAM memory device, with 8 rows per bank active and a refresh cycle time of 80 nanoseconds (versus 60 nanoseconds for a single row) with 4 banks in parallel and 16 nanosecond bank sequencing, the bandwidth would be 443 gigabytes/second. However, according to at least one embodiment of the present disclosure, with the wafer-on-wafer bond 206, with 32 rows per bank active, the refresh cycle time can approach 60 nanoseconds for 32 banks in parallel and without bank sequencing, the bandwidth is 5 terabytes/second using 8 watts. Such a significant bandwidth of data being sent from the memory device would overwhelm a typical interface and/or host device. However, certain logic devices (such as a DLA) can be configured to make use of that data bandwidth via the connections provided by the bond 206. Reduced off-chip movement of data can help reduce the power consumption associated with operating the memory in this fashion. Some embodiments of the present disclosure can provide, for example, a 70× performance increase in depthwise separable networks and/or a 130× performance increase on natural language processing (NLP)/recommendation systems as compared to some current solutions. When implemented in an edge server, for example, some embodiments of the present disclosure can provide 16-32× memory bandwidth versus current solutions.

Although not specifically illustrated, multiple memory die 202 can be stacked on one another via a bond analogous to the bond 206. Alternatively, or additionally, TSVs can be used for communication of data between or through stacked memory die 202. The bond pads between stacked memory die 202 can be at locations that are replicated on stacked memory die 202 in a vertical orientation (as illustrated) such that the stacked memory die 202 are in alignment. The stacked memory die 202 can be formed by a conventional process or by wafer-on-wafer bonding (between different memory wafers) in different embodiments.

Although not specifically illustrated, the die that is bonded to the substrate 208 (e.g., the memory die 202 (as illustrated) or the logic die 204) can have TSVs formed therein to enable communication with circuitry external to the memory die 202 and logic die 204. The TSVs can also be used to provide power and ground contacts. Compared to the contacts provided by wafer-on-wafer bonding, TSVs generally have greater capacitance and a larger pitch and do not have as great of a bandwidth.

Although not specifically illustrated, in some embodiments an additional component can be bonded to the system 200. For example, a thermal solution component can be bonded to the top of the logic die 204 to provide cooling for the system 200. The physically close connection between the logic die 204 and the memory die 202 may generate heat. The thermal solution can help dissipate heat for the system 200.

Although not specifically illustrated, in some embodiments an additional component (non-volatile memory) can be bonded to the system 200 (e.g., in order to persistently store a model for the ANN). However, in some embodiments, the non-volatile memory is not necessary because the models may be relatively small and frequently updated.

Figure 2B:
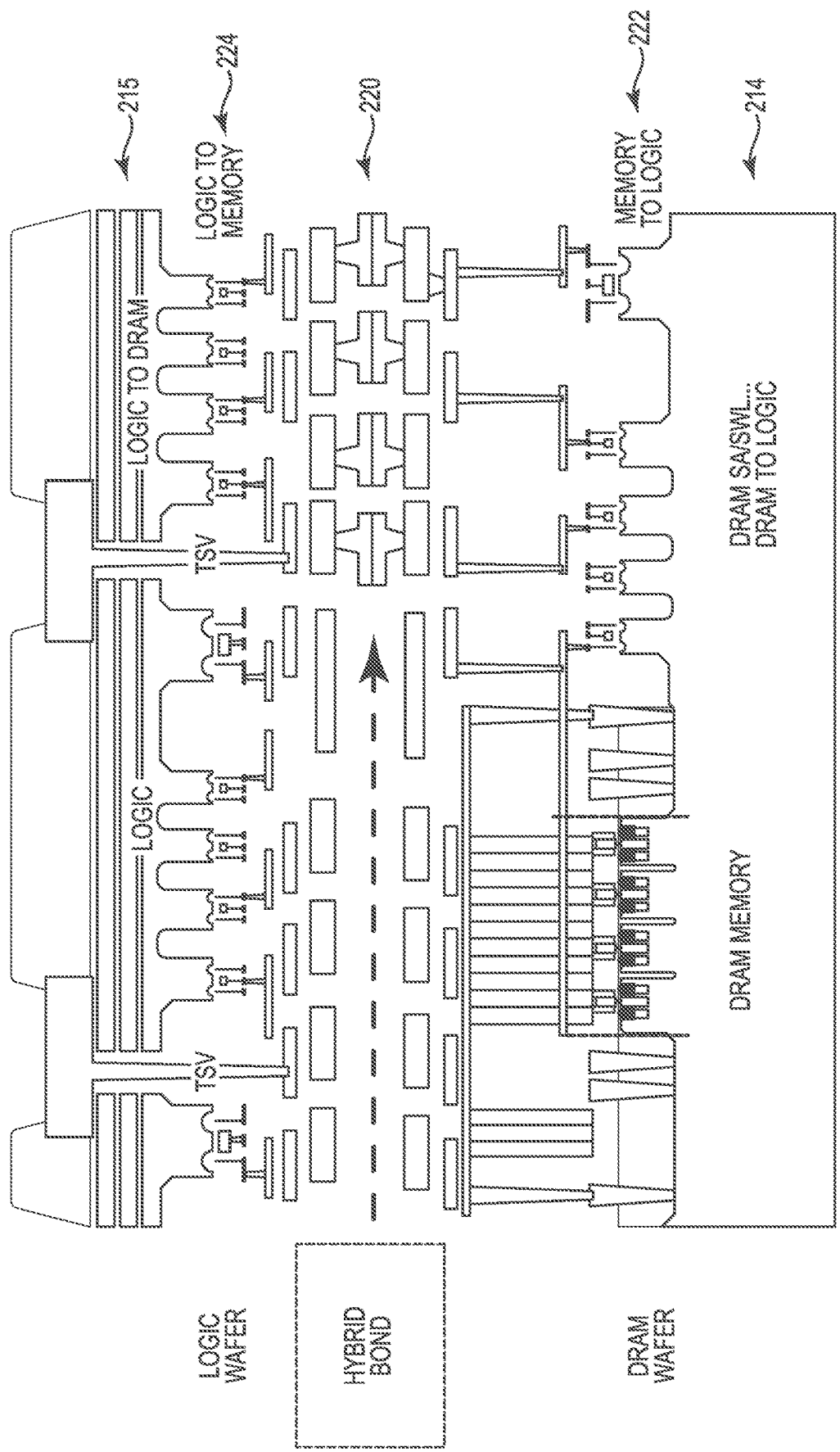
FIG. 2B illustrates a portion of bonded wafers including a memory die and a logic die in accordance with a number of embodiments of the present disclosure.

FIG. 2B is a cross-section of a portion of a memory wafer 214 bonded to the logic wafer 215 in accordance with a number of embodiments of the present disclosure. The memory wafer 214 includes memory-to-logic circuitry 222 formed thereon. The memory-to-logic circuitry 222 is configured to provide an electrical connection and signaling for the transfer of data and/or control signals between at least one memory die (e.g., memory die 202 of FIG. 2A) of the memory wafer 214 and at least one logic die (e.g., logic die 204 of FIG. 2A) of the logic wafer 215. In at least one embodiment, the memory-to-logic circuitry 222 can include as few as two additional metal layers beyond what is typically included for a DRAM memory die. The logic wafer 215 includes logic-to-memory circuitry 224 formed thereon. The logic-to-memory circuitry 224 is configured to provide an electrical connection and signaling for the transfer of data and/or control signals between at least one logic die of the logic wafer 215 and at least one memory die of the memory wafer 214. A bond 220 is formed between the memory-to-logic circuitry 222 of the memory wafer 214 and the logic-to-memory circuitry 224 of the logic wafer 215 in the wafer-on-wafer bonding process. The bond 220 may be referred to as a hybrid bond or a wafer-on-wafer bond herein. The bond 220 can include one or more of a metal bond and direct dielectric-dielectric bond. The bond 220 enables the transmission of electrical signals between the logic-to-memory circuitry 224 and the memory-to-logic circuitry 222.

The memory-to-logic circuitry 222 of the memory wafer 214 and/or the bond 220 can include bond pads at the transceiver, which can be associated with an LIO prefetch bus and/or sense amplifier (sense amp) stripe. In one example, one sense amp stripe includes 188 LIO connection pairs covering 9 array cores and 9216 pairs per channel. In another example, one sense amp stripe includes 288 LIO connection pairs and 4608 pairs per channel. Embodiments are not limited to these specific examples. The transceivers are described in more detail herein. The interconnect load of the bond 220 can be less than 1.0 femtofarads and 0.5 ohms. In one example implementation, the maximum number of rows of memory capable of being activated at one time (e.g., 32 rows) can be activated and transmit data via the bond 220 to the corresponding logic dies of the logic wafer 215. The memory-to-logic circuitry 222 and/or the bond 220 can include at least one power and at least one ground connection per transceiver (e.g., sense amp stripe). In at least one embodiment, the power connection is such that it allows activation of multiple rows of memory at once. In one example, the wafer-on-wafer bonding provides 256 k data connections at a 1.2 micrometer pitch.

In some embodiments, the bond 220 can include analog circuitry (e.g., jumpers) without transceivers in the path between the memory die 214 and the logic die 215. One die 214, 215 can drive a signal therebetween and the other die 214, 215 can sink the signal therebetween (e.g., rather than passing signals between the dies 214, 215 via logic gates). In at least one embodiment, the bond 220 can be formed by a low temperature (e.g., room temperature) bonding process. In some embodiments, the bond 220 can be further processed with an annealing step (e.g., at 300 degrees Celsius).

Although not specifically illustrated, in at least one embodiment a redistribution layer can be formed between the memory wafer 214 and the logic wafer 215. The redistribution layer can enable compatibility of a single memory design to multiple ASIC designs. The redistribution layer can enable memory technologies to scale without necessarily scaling down the logic design at the same rate as the memory technology (e.g., circuitry on the memory die 214 can be formed at a different resolution than the circuitry on the logic die 215 without having to adjust the bond 220 and/or other circuitry between the memory wafer 214 and the logic wafer 215).

Figure 3:
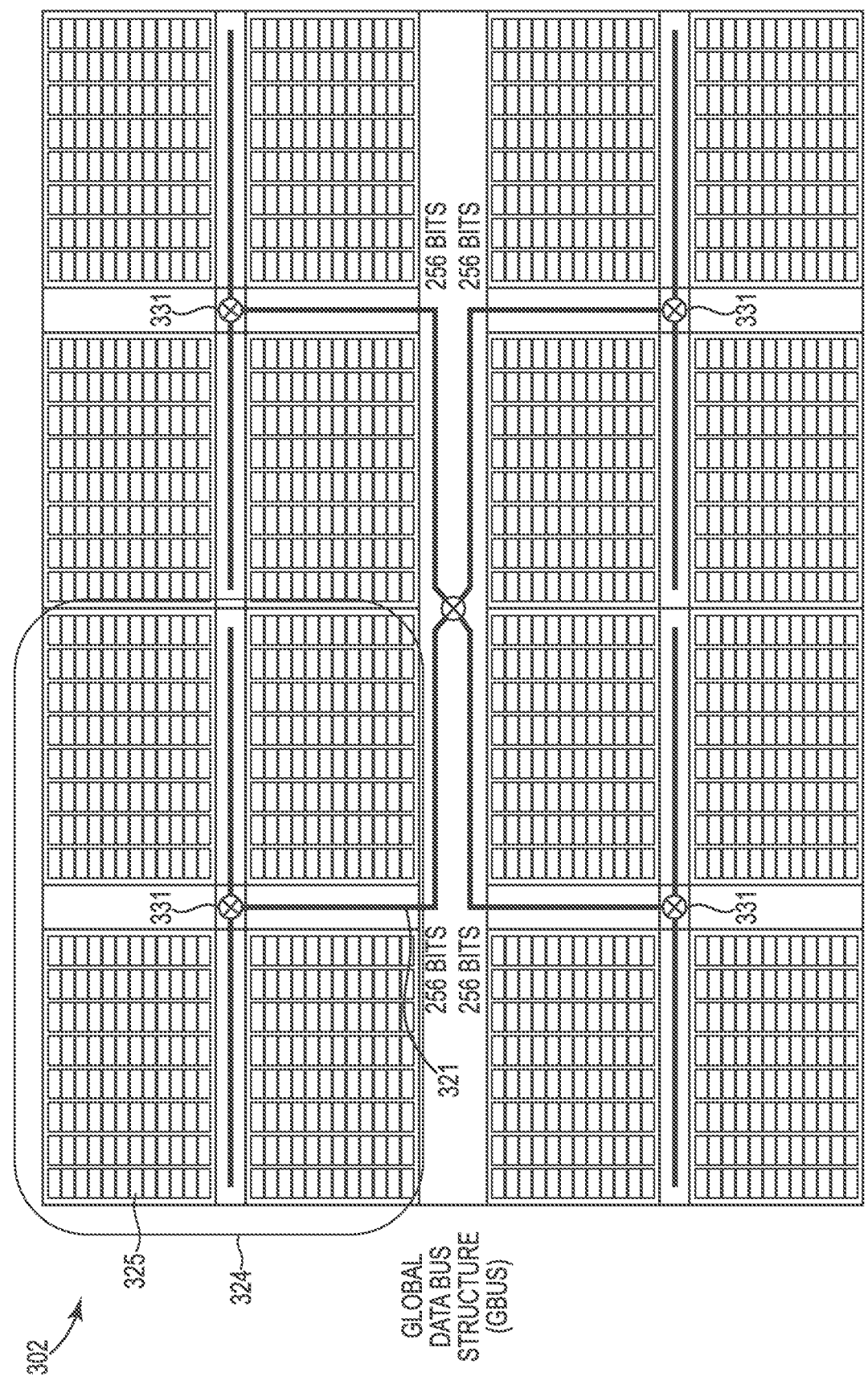
FIG. 3 illustrates a circuit diagram of a memory die in accordance with a number of embodiments of the present disclosure.

FIG. 3 illustrates a circuit diagram of a memory die 302 in accordance with a number of embodiments of the present disclosure. The example memory die 302 includes 16 memory banks 325 arranged in bank groups 324 of 4 banks. Each bank group 324 is coupled to a global data bus 321 (e.g., a 256 bit wide bus). Embodiments are not limited to these specific examples. The global data bus 321 can be modeled as a charging/discharging capacitor. The global data bus 321 can conform to a memory standard for sending data from the memory die 302 via an IO bus. However, although not specifically illustrated in FIG. 3, according to at least one embodiment of the present disclosure, the memory die 302 can include additional transceivers for communicating data with a logic die via a wafer-on-wafer bond.

FIG. 4 illustrates a memory bank 425 in accordance with a number of embodiments of the present disclosure. The memory bank 425 includes a quantity of memory tiles 433, each including a respective quantity of local IO lines 431 represented by the filled dots. Each tile 433 can include a quantity of rows and a quantity of columns of memory cells (e.g., 1024×1024). For example, each tile can include 32 LIOs 431. The LIOs 431 in each tile are coupled to a respective global IO line 432 and to a transceiver 462. The global IO lines 432 are coupled to the global data bus structure (GBUS) 421. The memory bank 425 can include additional transceivers (not shown) coupled to the LIOs 431 and/or the GBUS 421. The additional transceivers are selectively enabled to transmit data off-chip (e.g., to a logic die via a wafer-on-wafer bond) instead of to the corresponding global IO line 432. Multiple sense amplifiers can be multiplexed into a single transceiver 462 and to the additional transceivers. Each of the additional transceivers can be coupled to a respective contact with a corresponding logic die via a wafer-on-wafer bond. The additional transceivers can be incorporated in the logic die and/or the memory die. The wafer-on-wafer bond provides pitch control sufficiently fine to allow for such contacts, which would otherwise not be possible.

In at least one embodiment, the additional transceivers can receive an enable/disable command from the corresponding logic die coupled thereto (e.g., as opposed to receiving the command from a host). In some embodiments, the enable/disable command can be received by multiple additional transceivers (e.g., the enable/disable command can cause signals indicative of data from a particular row in each bank 425 to be transferred via the corresponding additional transceivers). The control and operation of the additional transceivers is similar to having thousands of memory controllers, except that they transfer data rather than controlling all operations. Such operation can be beneficial, for example, for applications that involve massively parallel memory access operations such as operations performed by networks. For an example memory device that is configured to include an 8 kilobit row, 256 bits of data can be prefetched per transceiver 462. Therefore, each additional transceiver can have 256 bits bonded out. In other words, at least one embodiment of the present disclosure can transfer 256 bits of data for each 8 kilobits of stored data (in this example architecture). In contrast, according to some previous approaches with an analogous architecture, a typical memory interface (e.g., via a global IO) would only be able to transfer 256 bits for 4 gigabits of stored data. The GBUS 421 can also be coupled to additional transceivers (e.g., other than multiplexor 331 in FIG. 3) configured to transfer data from the GBUS 421 to a logic die. However, data can be transferred from the GBUS 421 to the logic die at a lower rate utilizing the additional transceivers than the data is transferred from the LIO's 431 to the logic die utilizing the additional transceivers. For example, a full bandwidth of the GBUS 421 is 256 GBs while a full bandwidth of the LIOs is 65 TBs.

In various examples, signals can be routed from a memory die to a LIOs of the logic die. Signals can also be routed from the LIO of the logic die to the memory die. The signals can be routed between the memory die and the LIO of the logic die utilizing a transceiver of the memory die and/or a transceiver of the logic die.

In a number of examples, signals can be routed from the memory die to the logic die utilizing the LIOs 431 of the memory die. For example, signals can be routed from a memory array of the memory die to the LIOs 431 of the memory die. Signals can be routed from the LIOs 431 to LIOs of the logic die utilizing additional transceiver. The signals can be routed to enable the logic die to read data from the memory die. Signals can also be routed from the LIOs of the logic die to the LIOs of the memory die utilizing additional transceivers of the logic die and/or the memory die. The signals can be routed from the LIOs of the logic die to the LIOs 431 of the memory die to allow the logic die to write data to the memory die. The transceivers can be located in the memory die and/or the logic die. In various examples, the additional transceivers that are coupled to the LIOs 431 and that can be utilized to transfer data between the memory die and the logic die can be different from the additional transceivers that are coupled to the GBUS 421 which are also used to transfer data between the memory die and the logic die.

Figure 5A:
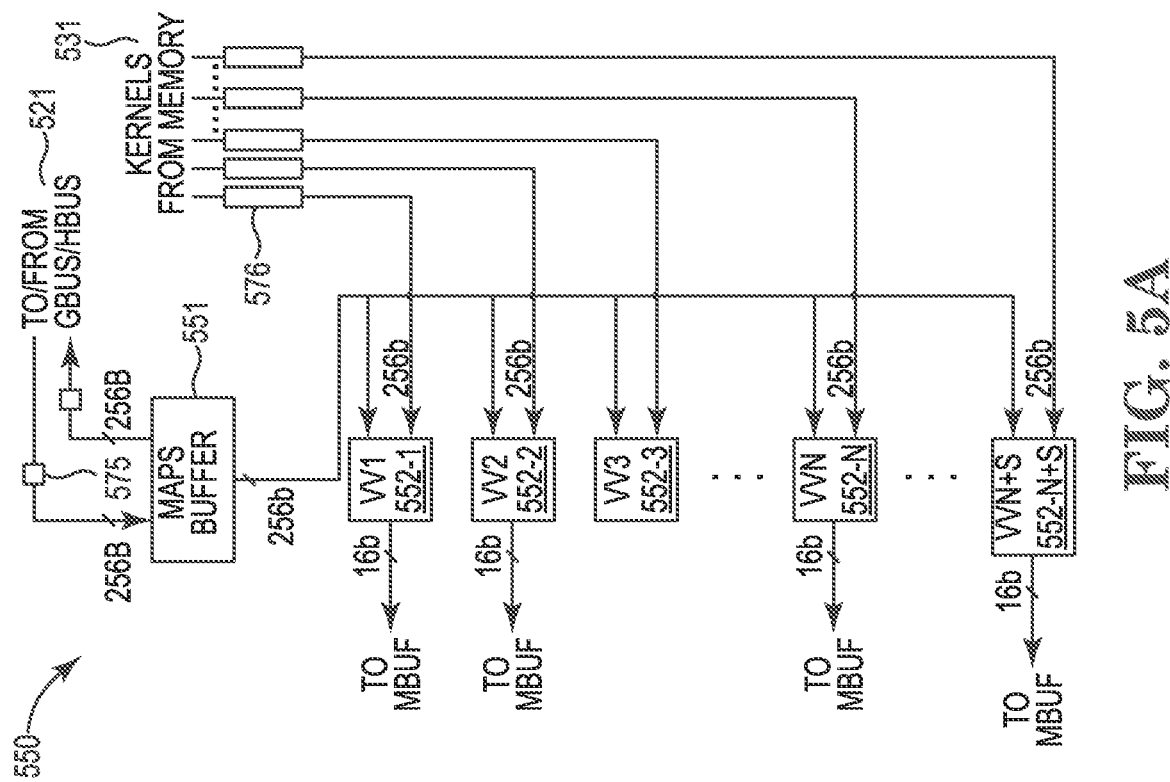
FIG. 5A illustrates a block diagram of vector-matrix circuitry for performing multiplication operations in accordance with a number of embodiments of the present disclosure.

FIG. 5A illustrates a block diagram of vector-matrix circuitry 550 for performing multiplication operations in accordance with a number of embodiments of the present disclosure. The logic die can comprise the circuitry 550, referred to herein as vector-matrix circuitry, for performing multiplication operations. A multiplication operation can utilize a vector and/or a matrix as operands. As used herein, a vector is a list of numbers in row or column while a matrix is an array of numbers comprising one or more rows and/or one or more columns. In the example of FIG. 5A the circuitry 550 can perform a multiplication operation utilizing a vector and a matrix as operands.

The multiplication operations can be utilized to implement a network. For example, multiplication operations implemented utilizing a vector and a matrix as operands can be utilized to implement different layers of a network (e.g., ANN). The multiplication operations implemented utilizing a vector and a matrix as operands can be utilized to implement a fully connected (FC) network. The multiplication operations implemented utilizing a vector and a matrix as operands can also be utilized to implement a long short-term memory (LSTM). A LSTM can be an artificial neural network that has feedback connections. A FC network can be an artificial neural network were each of the nodes of a layer are connected to all of the nodes of a next layer.

The circuitry 550 can comprise a buffer 551 and a plurality of vector-vector (VV) units 552-1, 552-2, 552-3, . . . , 552-N, . . . , 552-N+S which are referred to herein as VV units 552. The circuitry 550 can receive input data from a GBUS 521 of the memory die via transceivers 575 of the logic die. The input data can be received from a plurality of banks of the memory die. The buffer 551 is shown as "maps buffer" in FIG. 5. The maps buffer describes a buffer that is utilized to store input data. The term "maps" can be utilized to describe an input.

The circuitry 550 can receive kernel data from a plurality of LIOs 531 of the memory die via transceivers 576 of the logic die. The plurality of LIOs 531 can be referred to as an LBUS 531. As used herein, kernel data can include weights of a network or a type of parameter utilized in a network, among other applications of multiplication operations.

The input data received from the GBUS 521 can be stored in the buffer 551. The input data from the buffer 551 can be provided to the VV units 552. Each of the VV units 552 can receive the input data concurrently. Data can be received concurrently if the data is received at relatively the same time. In various examples, the input data can comprise 256 bits of data. The GBUS 521 can provide 256 bits of data which can be stored in the buffer 551. The 256 bits of the input data can be provided to the VV units 552 from the buffer 551 such that each of the VV units 552 receives a same 256 bits of input data.

Each of the VV units 552 can also receive 256 bits of kernel data. Each of the VV units 552 can receive a different 256 bits of the kernel data. For example, the VV unit 552-1 can receive 256 bits of the kernel data which can be different than the 256 bits of the kernel data which is received by the VV unit 552-2 which can be different from the bits received by the other VV units 552. More data can be provided to the VV units 552 from the LBUS 531 than is provided from the GBUS 521. The 256 bits of the kernel data can be received by the VV units 552 concurrently. In various examples, the kernel data can comprise a matrix of data while the input data can comprise a vector of data.

Each of the VV units 552 can output a vector which can be combined to constitute an output matrix. For example, each of the outputs of the VV units 552 can comprise 16 bits. Each of the MAC units of each of the VV units 552 can output 1 bit such that each of the VV units 552 outputs 16 bits. The outputs of the VV units 552 can be stored back to the buffer 551. The outputs can be moved from the buffer 551 to the memory die utilizing the logic-to-memory circuitry, the memory-to-logic circuitry, and the GBUS 521. For example, the output of the VV units 552 can be moved from the buffer 551 to the memory die utilizing the transceivers 575, of the logic die, which can be the same transceivers or different transceiver than the transceivers utilized to move data from the memory die to the logic die.

Although the GBUS 521 is shown as providing 256 bits, a GBUS 521 can have a different width such that it provides a different quantity of bits to the circuitry 550. The kernel data can also be provided via a data path having a different width than is shown. For example, each of the VV units 552 can receive a different quantity of bits than the 256 bits shown. The VV units 552 can also output a different quantity of bits than those shown (e.g., 16 bits outputted by each of the VV units 552).

Signals comprising the input data can be provided from the memory die utilizing a GBUS 521 and the memory-to-logic circuitry of the memory die. The signals comprising the input data can pass through the wafer-on-wafer bond to the logic-to-memory circuitry of the logic die. The signals comprising the input data can also pass from the logic-to-memory circuitry to a bus of the logic die and from the bus of the logic die to the buffer 551. The output data can be moved from the buffer 551 to the memory die by providing signals comprising the output data to the bus of the logic die, from the bus of the logic die to the logic-to-memory circuitry, and through the wafer-on-wafer bond. The signals comprising the output data can pass from the wafer-on-wafer bond to the memory-to-logic circuitry and from the memory-to-logic circuitry to the GBUS of the memory die. The signals comprising the output data can be provided from the logic die to the memory die utilizing transceiver of the logic die and/or the memory die. Once the signals arrive at the GBUS, the signals can be provided to the memory array or can be output from the memory die through an interface of the memory die that couples to the memory die to a host.

As used herein, the VV units 552 can comprise multiply accumulate (MAC) units, a shift register, an accumulator, and/or a precision modifier. The VV units 552 can also comprise MAC units, a shift register, a bias addresser, and/or a precision modifier. The MAC units can compute the product of two numbers and add that product to an accumulator utilizing the shift register. The MAC units can receive signals from a GBUS and/or an LBUS. The data received from the GBUS can be stored in a buffer and provided to the MAC units. The data received from the LBUS can be provided to the MAC units without being stored in a buffer. The accumulator of the VV units 552 can reduce the results of the MAC units into a single result or can add a value to the results of the MAC units. The precision modifier can modify the output of the accumulator to correspond to a format (e.g., position) that is needed. For example, the prevision modifier can modify the output of the accumulator to be in variable fix point. In various examples, the VV units 552 can operate in different modes such as a cooperation (COOP) mode or an independent mode to select a function of the MAC units, shift registers, accumulators, bias addresser and/or precision modifiers.

FIG. 5B illustrates a block diagram of vector-vector circuitry 550 for performing multiplication operations in accordance with a number of embodiments of the present disclosure. The logic die can comprise the circuitry 550, referred to herein as vector-vector circuitry, for performing multiplication operations. The type of multiplication operation described herein can include a multiplication operation performed utilizing a first vector and a second vector as operands. The multiplication operations that utilize vectors as operands can be utilized to implement a network. For example, performing the multiplication operations utilizing a plurality of vectors as operands can be utilized to implement different layers of a network (e.g., neural network).

The multiplication operations performed utilizing a plurality of vectors as operands can be utilized to implement a depthwise separable convolution neural network. The multiplication operations performed utilizing vectors as operands can be utilized to implement a depthwise convolution layer and/or a pointwise convolution layer of the depthwise separable convolution neural network.

The circuitry 550 comprises a buffer 551 and a plurality of VV units 552. The buffer 551 can be used to store data received from a GBUS 521. For example, the signals comprising kernel data can be received from the GBUS 521 of the memory die and can be stored in the buffer 551 of the logic die. Signals can be transferred from the GBUS 521 of the memory die to memory-to-logic circuitry of the memory die. The signals can be provided from the memory-to-logic circuitry to logic-to-memory circuitry of the logic die via a wafer-on-wafer bond.

The signals can be transferred from the logic-to-memory circuitry to the transceivers 575. The transceivers 575 can be activated to provide the signals to the buffer 551. The signals can be provided to the transceivers 757 utilizing the TSV's of the logic die. The signals can be provided from the transceivers 757 to the buffer 551 via the bus of the logic die.

The kernel data can comprise a vector. The kernel data can be provided from the buffer 551 to the VV units 552. For example, the kernel data can comprise 256 bits of data. The same 256 bits that comprise the kernel data can be provided to each of the VV units 552 concurrently.

Signals comprising input data can be provided to the VV units 552 from the LBUS 531 of the memory die. For example, a controller of the memory die can cause signals comprising the input data to be read from a memory array and provided to a plurality of LIOs, of the memory die, that comprise the LBUS 531. Signals comprising the input data can be transferred to a memory-to-logic circuitry of the memory die. The signals can further be transferred from the memory-to-logic circuitry of the memory die, through a wafer-on-wafer bond, to the logic-to-memory circuitry of the logic die. The signals that comprise the input data can be transferred from the logic-to-memory circuitry to transceivers 576 of the logic die via a plurality of TSVs and from the transceivers 576 to a bus of the logic die. The signals can be provided from the bus of the logic die to the VV units 552 without being first stored in a memory of the logic die such as one or more buffers.

Each of the VV units 552 can receive different signal that combined comprise the input data such that the input data is represented as a vector of data. In various instances, each of the lines providing signals that comprise the input data to the VV units 552 can provide a different portion of the signals that comprise the input data.

The signals that comprise the kernel data can be represented using 256 bits such that each of the VV units 552 receive the same 256 bits from the buffer 551. Each of the VV units 552 can also receive 256 bits of the input data. Each of the VV units 552 can output 256 bits such that the resultant output vector comprises 256 bits multiplied by the quantity of VV units. In various instances, the output data generated by the VV units can be provided to the memory die without being stored in a buffer such as the buffer 551. The signals comprising the output data can be moved via the transceivers 575, to a logic-to-memory circuitry of the logic die. The signals can be provided from the logic-to-memory circuitry to the memory-to-logic circuitry of the memory die via a wafer-on-wafer bond. The signals can be provided from the memory-to-logic circuitry of the memory die to a plurality of LIOs that comprise an LBUS 531.

The signals comprising the output data can be stored back to a memory array of the memory die or can be output to a host, for example. In various examples, the output data stored to the memory array can be utilized as input for future operations performed in a network. For instance, the output data can be provided back to the VV units 552 as input data or can be provided to different VV units from a different bank as input data.

Figure 6:
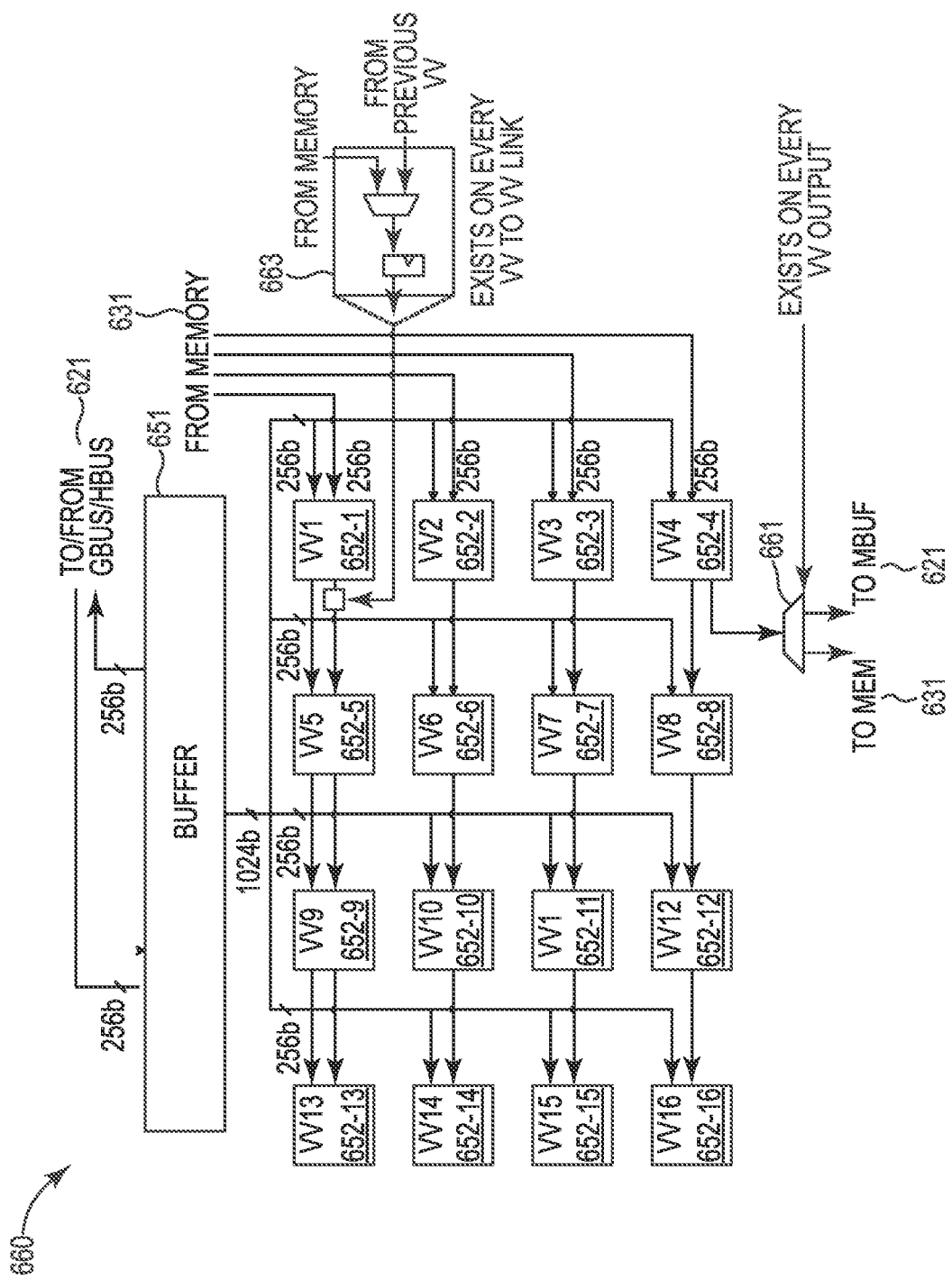
FIG. 6 illustrates a block diagram of a matrix-matrix (MM) unit for performing multiplication operations in accordance with a number of embodiments of the present disclosure.

FIG. 6 illustrates a block diagram of a matrix-matrix (MM) unit for performing multiplication operations in accordance with a number of embodiments of the present disclosure. The various examples, the circuitry 660 can be utilized to perform a multiplication operation utilizing a first matrix and a second matrix as operands. The circuitry 660 can comprise a buffer 651, and VV units 652-1, 652-2, 652-3, 652-4, 652-5, 652-6, 652-7, 652-8, 652-9, 652-10, 652-11, 652-12, 652-13, 652-14, 652-15, 652-16, referred to as VV units 652. The circuitry 660 can also include input circuitry 663 and output circuitry 661. The circuitry 660 can also be referred to as the MM unit.

In various instances, data can be received from a GBUS 621 of the memory die via a plurality of transceivers (e.g., transceivers 575 of FIGS. 5A, 5B). Data can also be received from an LBUS 631 of the memory die via a plurality of transceivers (e.g., transceivers 576 of FIGS. 5A, 5B). The data received from the GBUS 621 of the memory die can be stored in the buffer 651. In various instances, the data received by the buffer 621 can be received over various clock cycles. For example, a first portion of a matrix can be received in a first number of clock cycles while a second portion of a matrix can be received in a second number of clock cycles.

The data received from the LBUS 631 can be received directly from the LBUS 631 without being stored in a buffer and/or a plurality of buffers prior to being provided to the VV units 652. Although the circuitry 660 can be utilized to perform multiplication operations utilizing a first matrix and a second matrix as operations, the circuitry 660 can also be utilized to perform multiplication operations utilizing vectors as operands and/or a vector and a matrix as operands. For instance, only a portion of the VV units 652 can be utilized to perform multiplication operations utilizing vectors as operands and/or a vector and a matrix as operands Although the circuitry 660 can be utilized to perform multiplication operations utilizing vectors as operations and/ or a vector and a matrix as operands the circuitry 660 may utilized more efficiently to perform multiplication operations utilizing a first matrix and a second matrix as operands.

In the example provided in FIG. 6, the buffer 651 can provide multiple portions of a matrix to the VV units 652. For example, the buffer 651 can provide a first portion of matrix to the VV units 652-1, 652-2, 652-3, 652-4. The buffer 651 can provide a second portion of the matrix to the VV units 652-5, 652-6, 652-7, 652-8. The buffer 651 can provide a third portion of the matrix to the VV units 652-9, 652-10, 652-11, 652-12. The buffer 651 can provide a fourth portion of the matrix to the VV units 652-13, 652-14, 652-15, 652-16. In various examples, the first, second, third, and fourth portions of a matrix can comprise a first, second, third, and fourth row of a matrix or columns of a matrix, respectively.

The data received from the LBUS 631 of the memory die can be provided to the VV units 652 without being stored in a buffer such as buffer 651. In various examples, each of the VV units 652 can receive 256 bits. For example, a number of the VV units 652-1, 652-5, 652-9, 652-13 can receive a first portion of a matrix provided from the LBUS 631 which comprises 256 bits. A number of the VV units 652-2, 652-6, 652-10, 652-14 can also receive a second portion of the matrix provided from the LBUS 631. A number of the VV units 652-3, 652-7, 652-11, 652-15 can receive a third portion of the matrix provided from the LBUS 631. A number of the VV units 652-4, 652-8, 652-12, 652-16 can receive a fourth portion of the matrix provided from the LBUS 631. The first, second, third, and forth portions of the matrix provided form the LBUS 631 can comprise rows or columns of the matrix.

In various examples, the VV unit 652-1 can receive a first portion of the matrix received, which is referred to as a second matrix, from the LBUS 631, the VV unit 652-2 can receive a second portion of the second matrix, the VV unit 652-3 can receive a third portion of the second matrix, and the VV unit 652-4 can receive a fourth portion of the second matrix. The VV unit 652-1 can also receive a first portion of the matrix, which is referred to as a first matrix, received from the GBUS 62, the VV unit 652-2 can receive a second portion of the first matrix, the VV unit 652-3 can receive a third portion of the first matrix, and the VV unit 652-4 can receive a fourth portion of the first matrix. The outputs of the VV units 652 can be provided to an output circuitry 661 and an input circuitry 663.

The input circuitry 663 can exists between each of the VV units 652. For example, the input circuitry 663 can be coupled to the VV unit 652-1 and the VV unit 652-5 and a different input circuitry (not shown) can be coupled to the VV unit 652-2 and the VV unit 652-6, etc. The input circuitry 663 can comprise a multiplexer (MUX) which can be used to select whether a portion of the second matrix (e.g., matrix provided from the LBUS 631) is provided to a next VV unit or whether an output of a previous VV unit is provided to the next VV unit. For instance, the MUX of the input circuitry 663 can be controller by a controller of the logic die to provide a first portion of the second matrix to the VV unit 652-5 or an output of the VV unit 652-1.

The output circuitry 661 can comprise a different MUX which is used to determine to where to provide the output of the VV units 652. Each of the VV units 652 is coupled to a different output circuitry (e.g., output circuitry 661). For example, the output circuitry 661 can receive an output of the VV unit 652-4. The controller of the logic die can cause the output circuitry 661 to provide the output of the VV unit 652-4 to an LBUS 631 of the memory die or the buffer 651. Providing an output to the buffer 651 can cause the output to be provided to the GBUS 621 of the memory die.

In various examples, each of the VV units 652 can receive 256 bits from a first matrix and 256 bits from a second matrix concurrently. In some examples, each group of VV units 652 can receive 256 bits from a first matrix and 256 bits from a second matrix or from an output of a previous VV unit concurrently. For instance, the VV units 652-1, 652-2, 652-3, 652-4 can receive 256 bits of the first matrix and a different portion of the second matrix (e.g., a first portion, a second portion, third portion, and a fourth portion of the second matrix) concurrently. The VV units 652-5, 652-6, 652-7, 652-8 can receive different 256 bits of the first matrix and an output of a previous VV unit (e.g., the VV units 652-1, 652-2, 652-3, 652-4) or a different portion of the second matrix (e.g., a first portion, a second portion, third portion, and a fourth portion of the second matrix) concurrently. The VV units 652-9, 652-10, 652-11, 652-12 can receive different 256 bits of the first matrix and an output of a previous VV unit (e.g., the VV units 652-5, 652-6, 652-7, 652-8) or a different portion of the second matrix (e.g., a first portion, a second portion, third portion, and a fourth portion of the second matrix) concurrently. The VV units 652-13, 652-14, 652-15, 652-16 can receive different 256 bits of the first matrix and an output of a previous VV unit (e.g., the VV units 652-9, 652-10, 652-11, 652-12) or a different portion of the second matrix (e.g., a first portion, a second portion, third portion, and a fourth portion of the second matrix) concurrently.

In various instances, the circuitry 660 can comprise more or less VV units than those shown herein. For example, the circuitry 660 can comprise more than 16 VV units or less than 16 VV units.

The VV units 652 can receive portions of the second matrix provided from the LBUS such that each VV unit can receive different portions at different times. For example, at a first time, the VV unit 652-1 can receive a first portion of the second matrix while at a second time the VV unit 652-2 can receive a seventeenth portion of the second matrix, etc. until all of the portions of the second matrix have been provided to the VV units 652. This arraignment can be utilized when there are more portion of the second matrix than there are rows of VV units.

The matrices can be received from the GBUS 621 and the LBUS 631 as previously discussed. For example, signals comprising a first matrix can be received at the buffer 651 of the logic die from the GBUs 621 of the memory die as previously discussed in FIGS. 4 and 5. Signals comprising a second matrix can be received at the VV units 652 as previously discussed in FIGS. 4 and 5.

Figure 7:
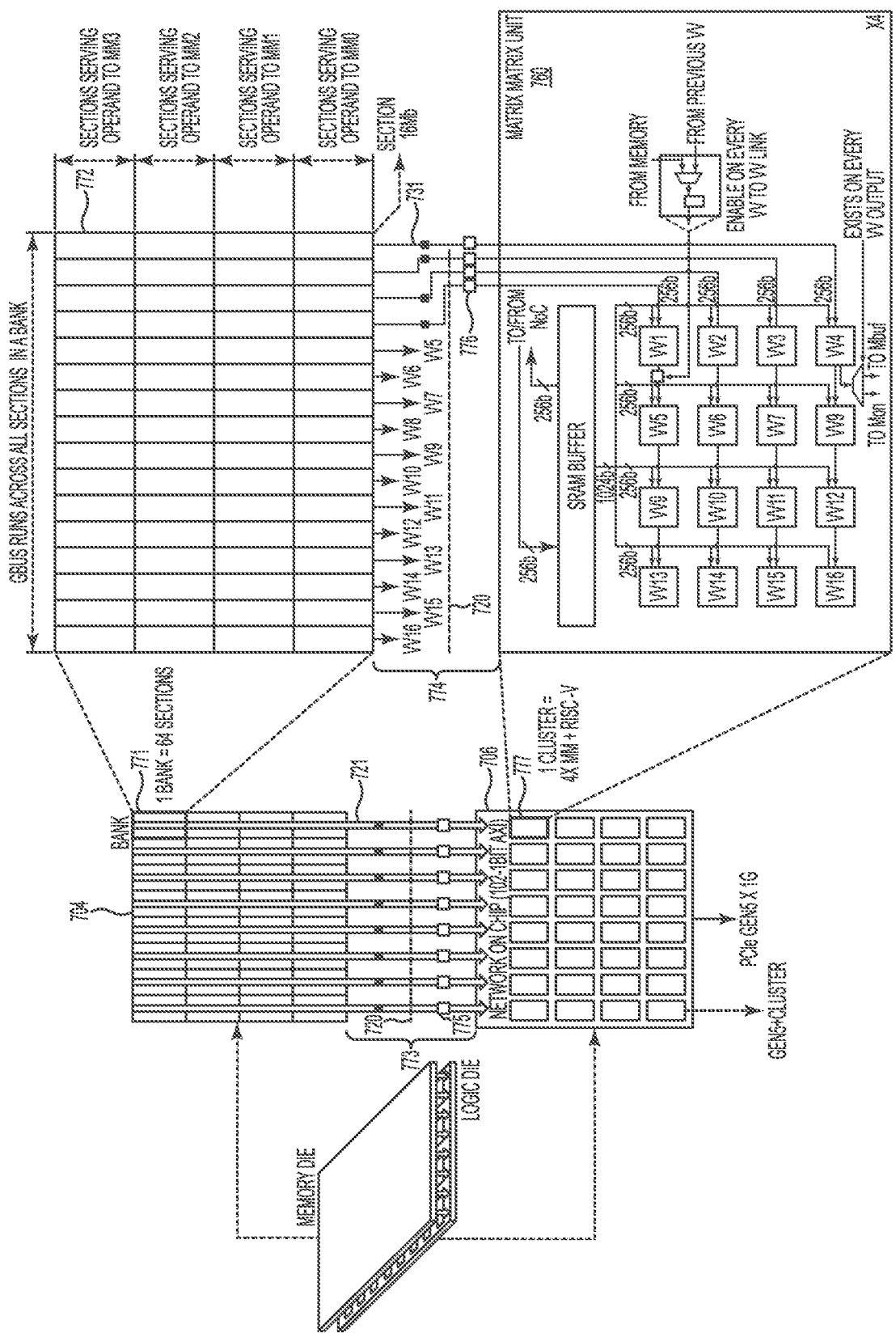
FIG. 7 illustrates a block diagram of a memory array for performing multiplication operations in accordance with a number of embodiments of the present disclosure.

FIG. 7 illustrates a block diagram of a memory array 704 for performing multiplication operations in accordance with a number of embodiments of the present disclosure. FIG. 7 includes a memory die including the memory arrays 704 and a hardware 706 of the logic die. The hardware 706 can be, for example, a network (e.g., network on chip).

The memory arrays 704 can subdivided into banks 771. Each of the banks can include sections 772. For example, the memory die can include 32 banks 704 and each of the 32 banks 704 can be comprised of 64 sections 772. However, more or less banks 704 and/or sections 772 can be included in the memory die.

The hardware 706, which can also be referred to as a network 706, can be comprised of MM units 760. Each of the MM units 760 can be comprised of VV units as described in FIG. 6. Although the hardware 706 is shown as being comprise of MM units 760, the hardware 706 can be comprised of vector-vector circuitry, vector-matrix circuitry, and/or MM units 760. The network 706 can comprise 32 clusters of MM units. Each cluster of MM units can be comprise, for example, of 4 MM units 760.

In various examples, the banks 771 can be coupled to the network 706. Each of the banks 771 can be coupled to a GBUS 721 of the memory die. The logic die can also be coupled to the GBUS 721 via a wafer-on-wafer bond 720. For example, the logic die can be coupled to the GBUS 721 via a memory-to-logic circuitry of the memory die, a logic-to-memory circuitry of the logic die, and the wafer-on-wafer bond 720. A controller of the logic die can activate the transceivers 775, of the logic die, to provide signals from the GBUS 721 to the network 706. A controller of the logic die can also activate the transceivers 775 to provide signals from the network 706 to a GBUS 721 of the memory die.

Signals received from the GBUS 721 can originate from the banks 771 coupled to the GBUS 721. For example, if four banks provide data to the logic die via a first line of the GBUS 721, then a plurality of clusters 777 coupled to the first line can access the data, while a different plurality of clusters 777 coupled a second line of the GBUS 721 can access data from different banks (e.g., different four banks) also coupled to the second line of the GBUS 271.

A controller of the logic die can activate the transceivers 775 to provide data from the GBUS 721 to the network 706. The dots on the GBUS 721 denote a connection of a line of the memory die to the GBUS 721, where the line couples the transceivers 775 to the GBUS 721 indefinitely. While the GBUS 721 can be utilized to provide signal via a traditional IO circuitry of the memory die, the line coupled to the GBUS 721 can be utilized to provide data to the logic die from the GBUS 721. The transceivers 775 can cause signals to be provided to buffers of the MM units 760, to buffers of the vector-matrix circuitry shown in FIG. 5A, and/or the VV units of the vector-vector circuitry shown in FIG. 5B.

The logic die can also receive signals from an LBUS 731. For example, lines of the memory die can couple the LBUS 731 to a logic die via the wafer-on-wafer bond 720. In various instances, the lines that coupled the LBUS 731 or the GBUS 721 to the logic die can be included in the memory-to-logic circuitry of the memory die. The transceivers 776 of the logic die can be activated to cause the signals from the LBUS 731 to be provided to the network 706. Each of the MM units 760 can be coupled to a portion of the sections 772 of a bank 771 such that each of the MM units 760 of the network 721 can receive signals from a different portion of the sections 772. A first MM unit of a cluster 777 can receive signals from a first plurality of sections, a second MM unit of the cluster 777 can receive signals from a second plurality of sections, a third MM unit of the cluster 777 can receive signals from the third plurality of sections, and/or a fourth MM unit of the cluster 777 can receive signals from the fourth plurality of sections, wherein the first plurality of sections, the second plurality of sections, third plurality of section, and the fourth plurality of sections comprise the bank 771.

Each of the sections can provide signals to a particular VV unit of the MM unit 760. For instance, a first section of the first plurality of sections of a bank can provide signals to a first VV unit of a first MM unit 760 of a cluster of MM units. A first transceiver can allow signals to be provided to the first VV units from a first line of the LBUS 731. A second section of the first plurality of sections may not provide signals to the first MM unit 760 because the first transceiver may be configured to provide signals from the first line of the LBUS 731 and not a second lien of the LBUS 731 which can be utilized to provide signals from the second section of each of the plurality of sections to second VV units from the MM units 760 of a cluster of the network 706. The transceivers 776 can cause signals to be provided to the VV units of the MM unit, to the VV units of the vector-matrix circuitry of FIG. 5A, and/or to the buffers of the vector-vector circuitry of FIG. 5B.

In various instances, the network 706 can include the MM units 760, as shown, the vector-matrix circuitry of FIG. 5A, and/or the vector-vector circuitry of FIG. 5B. For example, the clusters 777 can be comprised of MM units 760, vector-matrix circuitry, and/or the vector-vector circuitry.

The network 706 can be configured to perform multiplication operations consistent with a layer of an artificial network utilizing the MM units 760, the vector-matrix circuitry, and/or the vector-vector circuitry. The network 706 can implement a convolution layer, a maxpool layer (e.g., spatial pooling layer/depthwise separable layer), or a fully connected network of an artificial network, among other possible layer of an artificial network. Although the hardware 706 is identified as a network, the hardware 706 can be configured to perform multiplication operations regardless of whether the multiplication operations are utilized in artificial networks or different types of learning constructs.

Figure 8:
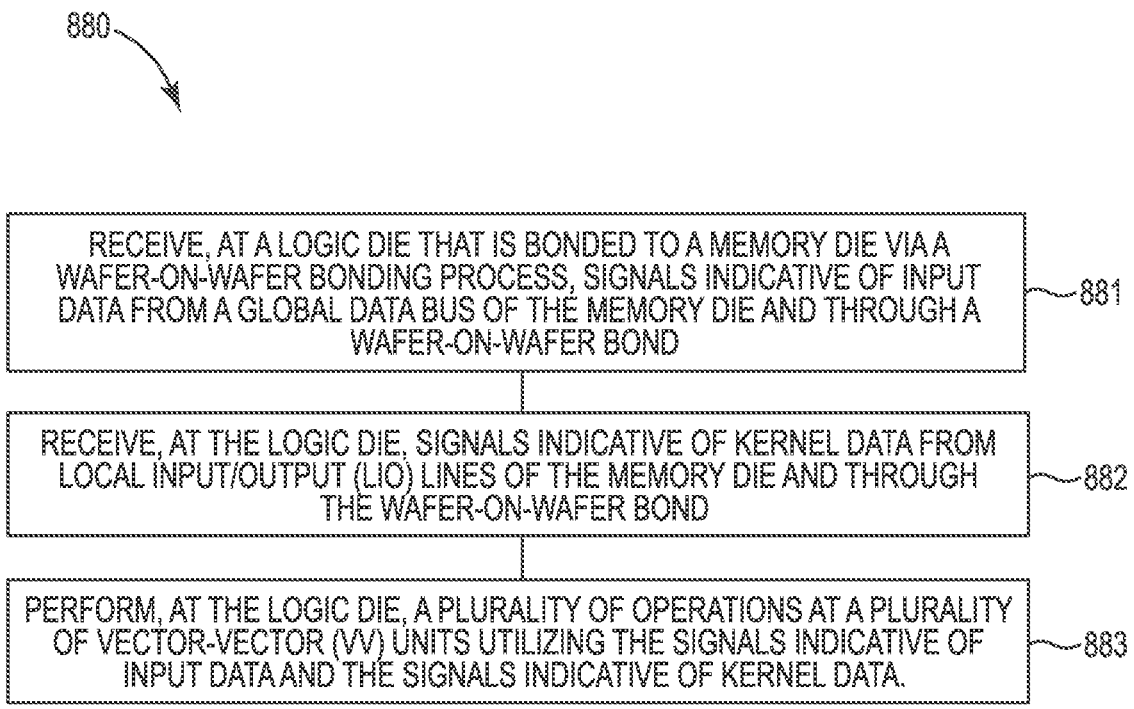
FIG. 8 is a flow diagram corresponding to a method for routing signals between a memory die and a logic die in accordance with some embodiments of the present disclosure.

FIG. 8 is a flow diagram corresponding to a method 870 for routing signals between a memory die and a logic die in accordance with some embodiments of the present disclosure. At operation 881, signals indicative of input data can be received from a global data bus of the memory die and through a wafer-on-wafer bond, where the signals are received at a logic die that is bonded to a memory die via a wafer-on-wafer bonding process. At operation 882, signals indicative of kernel data can be received, at the logic die, from local input/output (LIO) lines of the memory die and through the wafer-on-wafer bond. At operation 883, a plurality of operations can be performed at a plurality of vector-vector (VV) units utilizing the signals indicative of input data and the signals indicative of kernel data. The plurality of operations can be performed at the logic die.

In various instances, receiving signals indicative of the input data can further comprise storing, at a buffer of the logic die, the input data received as the signals indicative of the kernel data. Receiving signals indicative of the kernel data can further include transferring the signals indicative of the kernel data from the buffer to the plurality of VV units. In various examples, each of the VV units can receive a same data of different data from the buffer. Signals indicative of output data generated by performing the plurality of operations can be stored in the buffer.

The plurality of operations can be performed at the plurality of VV units. Each of the plurality of VV units can receive the signals indicative of the kernel data from the buffer concurrently. In various examples, portions of the plurality of VV units can receive the signals indicative of the kernel data from the buffer concurrently while different portions of the plurality of VV units receive the signals sequentially from the receipt of the signals at the portion of the plurality of VV units.

Each of the plurality of VV units can receive a plurality of different signals indicative of a different portion of the kernel data from the LIO lines. The input data can comprise a quantity of bits that is less than or equal to a different quantity of bits that comprises the kernel data. The input data can comprise a same quantity of bits as each of the different portions of the kernel data.

In various examples, a logic die can be bonded to the memory die via a wafer-on-wafer bonding process. The logic die can comprise VV units. The VV units can be configured to receive signals indicative of kernel data from a GBUS of the memory die and through a wafer-on-wafer bond. The signals can be received by activating a transceiver coupled to the GBUS. Wherein the transceiver in part of the logic die. The VV units can receive signals indicative of input data from LIO lines of the memory die and through the wafer-on-wafer bond. The signals indicative of the input data can be received by activating different transceivers of the logic die. The VV units can perform a plurality of operations using the signals indicative of kernel data and the signals indicative of input data. The VV units can provide a result of the plurality of operations to the LIO lines of the memory die.

The VV units can further be configured to provide the result of the plurality of operation to the LIO lines via the wafer-on-wafer bond. The result can be provided to the LIO lines by activating the plurality of different transceivers.

The logic die can receive the signals indicative of the kernel data and the signals indicative of the input data via logic-to-memory circuitry of the logic die that is bonded to the memory die via the wafer-on-wafer bond. The logic die can receive the signals indicative of the kernel data and the signals indicative of the input data via memory-to-logic circuitry of the memory die that is bonded to the logic die via the wafer-on-wafer bond.

The logic die can receive the signals indicative of the kernel data and the signals indicative of the input data via a plurality of lines generated via the wafer-on-wafer bonding process that couple the LIO lines and the GBUS to TSVs. The VV units can receive the signals indicative of the kernel data and the signals indicative of the input data from the TSVs. In various examples, each of the plurality of VV units can receive the signals indicative of the input data via from a different section of a bank of the memory die via different LIO lines coupled to the different section.

In various instances, a first plurality of VV units, of the logic die, can receive signals indicative of a first portion of first data from a GBUS of the memory die and through a wafer-on-wafer bond. The signals indicative of a second data can be received from the memory die from local input/output (LIO) lines of the memory die and through the wafer-on-wafer bond. A first plurality of operations can be performed using the signals indicative of the first portion of the first data and the signals indicative of the second data to generate first output data. A second plurality of VV units, of the logic die, can comprise a second plurality of VV units. The second plurality of VV units can receive signals indicative of a second portion of the first data from the GBUS through the wafer-on-wafer bond. The second plurality of VV units can also receive signals indicative of the first output data, of the first plurality of operations, from first plurality of VV units. The second plurality of VV units can also perform a second plurality of operations using the signals indicative of the second portion of the first data and the signals indicative of the output data to generate second output data. The first plurality of operations and the second plurality of operations can output signals indicative of first output data and the second output data to the LIO lines or the GBUS.

The first plurality of VV units can receive the signals indicative of the first portion of the first data where the first portion of the first data comprises a portion of kernel data. The first plurality of VV units can also receive the signals indicative of the second data wherein the second data comprises input data. The second plurality of VV units can receive the signals indicative of the second portion of the first data wherein the second portion of the first data comprises a different portion of the kernel data.

The first plurality of VV units can receive the signals indicative of the first portion of the first data where the first portion of the first data comprises a portion of input data. The first plurality of VV units can also receive the signals indicative of the second data wherein the second data comprises kernel data. In various examples, the second plurality of VV units can receive the signals indicative of the second portion of the first data where the second portion of the first data comprises a different portion of the input data.

As used herein, "a number of" something can refer to one or more of such things. For example, a number of memory devices can refer to one or more memory devices. A "plurality" of something intends two or more.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:
1. A method comprising:
 receiving, at a logic die that is bonded to a memory die via a wafer-on-wafer bonding process, signals indicative of input data from a global data bus of the memory die and through a bond of the logic die and memory die;
 receiving, at the logic die, signals indicative of kernel data from local input/output (LIO) lines of the memory die and through the bond; and performing, at the logic die, a plurality of operations at a plurality of vector-vector (VV) units utilizing the signals indicative of input data and the signals indicative of kernel data.

2. The method of claim 1, wherein receiving signals indicative of the input data further comprises storing, at a buffer of the logic die, the input data received as the signals indicative of the kernel data.

3. The method of claim 2, wherein receiving signals indicative of the kernel data further comprises, transferring the signals indicative of the kernel data from the buffer to the plurality of VV units.

4. The method of claim 2, further comprising storing signals indicative of output data generated by performing the plurality of operations in the buffer.

5. The method of claim 1, wherein performing the plurality of operations further comprises performing the plurality of operations at the plurality of VV units, and wherein each of the plurality of VV units receives the signals indicative of the kernel data from the buffer concurrently.

6. The method of claim 1, wherein performing the plurality of operations further comprises performing the plurality of operations at the plurality of VV units, and wherein each of the plurality of VV units receives a plurality of different signals indicative of a different portion of the kernel data from the LIO lines.

7. The method of claim 6, wherein the input data comprises a quantity of bits that is less than or equal to a different quantity of bits that comprises the kernel data.

8. The method of claim 7, wherein the input data comprises a same quantity of bits as each of the different portions of the kernel data.

\* \* \* \* \*